(12) United States Patent
Ryan

(10) Patent No.: US 6,391,033 B2
(45) Date of Patent: *May 21, 2002

(54) SOLUBLE FIXATION DEVICE AND METHOD FOR STENT DELIVERY CATHETERS

(75) Inventor: Timothy James Ryan, Portola Valley, CA (US)

(73) Assignee: Thomas J. Fogarty (*) Notice: Subject to any disclaimer, the term of this patent is extended or adjusted under 35 U.S.C. 154(b) by 0 days.

This patent is subject to a terminal disclaimer.

(21) Appl. No.: 09/753,121

(22) Filed: Jan. 2, 2001

Related U.S. Application Data

(63) Continuation of application No. 09/185,867, filed on Nov. 3, 1998, now Pat. No. 6,168,602, which is a continuation of application No. 08/694,717, filed on Aug. 9, 1996, now Pat. No. 5,830,217.

(51) Int. Cl.[7] .................................................. A61F 11/00
(52) U.S. Cl. ..................... 606/108; 604/263; 604/265; 623/1.11; 623/1.46
(58) Field of Search .......................... 606/108; 604/263, 604/265, 287, 288; 623/1.11, 1.12, 1.44, 1.46, 1.47, 1.48

(56) References Cited

U.S. PATENT DOCUMENTS

| 3,736,939 | A | | 6/1973 | Taylor ........................ 604/265 |
|---|---|---|---|---|
| 4,306,563 | A | | 12/1981 | Iwatschenko ................ 604/265 |
| 4,827,940 | A | | 5/1989 | Mayer et al. ................ 604/265 |
| 4,906,237 | A | | 3/1990 | Johansson et al. .......... 604/265 |
| 5,576,072 | A | | 11/1996 | Hostettler et al. ........... 427/532 |
| 5,697,967 | A | * | 12/1997 | Dinh et al. ................. 623/1.11 |
| 5,830,217 | A | * | 11/1998 | Ryan .......................... 606/108 |

FOREIGN PATENT DOCUMENTS

EP 615769 9/1994 ................. 604/265

* cited by examiner

Primary Examiner—Michael J. Milano
Assistant Examiner—Julian W. Woo
(74) Attorney, Agent, or Firm—K. David Crockett, Esq.; Crockett & Crockett

(57) ABSTRACT

A soluble capsule, fairing or adherent material for a stent catheter or other device to inserted into the human body. The capsule, fairing or adherent material is made of a material which dissolves within the body in a convenient time, for example ten or fifteen minutes, allowing a convenient time for placement of the device and protecting the blood vessel from any sharp surfaces of the device.

7 Claims, 1 Drawing Sheet

SOLUBLE FIXATION DEVICE AND METHOD FOR STENT DELIVERY CATHETERS

This application is a continuation of U.S. application Ser. No. 09/185,867 filed Nov. 3, 1998, now U.S. Pat. No. 6,168,602, which is a continuation of U.S. application Ser. No. 08/694,717 filed Aug. 9, 1996, now U.S. Pat. No. 5,830,217.

FIELD OF THE INVENTIONS

This invention relates to catheters and intraluminal delivery devices.

BACKGROUND OF THE INVENTIONS

There are many devices used to treat vascular diseases which require introduction of catheters and catheter based devices into the blood vessels. Blockages of the coronary arteries and peripheral arteries such as the femoral artery, iliac artery, and carotid artery can be treated or cured by placement of stents which keep arteries open. Blockages can also be cured, at least temporarily, with angioplasty balloons, atherectomy devices, endarterectomy devices, and embolectomy devices. Aneurysms of the aorta, femoral artery, carotid artery and other arteries can be treated with the placement of stent grafts into the artery which isolate the aneurysm from the blood stream. Placement of these devices is accomplished percutaneously by inserting the catheter into a remote peripheral blood vessel such as the femoral artery in the groin (the femoral, carotid, or subclavian arteries are frequently used), and then snaking the tip of the catheter to the diseased portion of the artery. For example, a catheter can be placed into the coronary arteries through a circuitous route from the femoral artery, up the aorta, over the aortic arch, and turning into any of the coronary arteries which communicate with the aorta. Likewise, a graft may be placed in the aorta through a percutaneous puncture in the femoral artery in the thigh or the carotid artery in the neck. Catheter based stents, probes, etc. may be used in other tortuous body lumens such as the urethra, ureter, biliary ducts, and fallopian tubes.

Many diagnostic and device deployment catheters have sharp or irregular contours which can damage the inside wall of blood vessels when the devices pass through the blood vessel and scrape the sides of the blood vessel. For example, stents used for coronary arteries are typically expanded metal stents mounted on balloon catheters, with the stent surrounding the balloon, and the balloon tightly compacted within the stent. The outer contours of these balloon mounted stents can be quite sharp and irregular, and damage caused to the inside wall of blood vessels is common. The damage caused to blood vessels during stent deployment can lead to further occlusion of the vessel as the blood vessel heals.

The placement of stents, ultrasound imaging catheters, angioplasty balloon, angiography contrast medium injection catheters and the like generally requires (1) percutaneous puncture of a large artery such as the femoral artery with a large needle (2) insertion of an introducer sheath through the puncture, (3) insertion of a guidewire through the introducer sheath into the artery (4) steering the guidewire through the vasculature until it is near, or slightly past, the diseased portion of a blood vessel and (5) mounting a diagnostic catheter or treatment catheter on the guidewire and pushing the catheter along the guidewire until it reaches the diseased portion of the blood vessel. For some applications, additional sheaths may be used, such as the doogie sometimes used to prevent the hemostasis valve from dislodging or damaging the stent during insertion. Each of these introductions involves passage of blunt or irregular objects along the inner surface of blood vessels, which can cause damage to the intima or inner wall of the blood vessels.

The problem of intimal damage is especially apparent in stent deployment catheters. Stents are commercially available in several forms, and many others have been proposed in patents and the medical literature. The Palmaz™ stent is a expandable metal stent mounted on an angioplasty balloon (the stent is sometimes sold separately from the angioplasty balloon). The Palmaz-Schatz™ stent is similar to the Palmaz™ stent, with several stent sections linked together. These stents are often used to treat stenosis and blockage of the coronary arteries. The stent proposed by Beck, Device for the Widening of Blood Vessels, U.S. Pat. No. 4,877,930 (Oct. 31, 1989) is made of a rolled frame mounted on a balloon, with exposed sharp edges. Wiktor, Intracoronary Stent and Method of Simultaneous Angioplasty and Stent Implant, U.S. Pat. No. 4,969,458 (Nov. 13, 1990) shows a "notebook binding" type wire stent mounted on a balloon, with exposed irregular surfaces. Very similar structure is disclosed in Gianturco, Endovascular Stent and Delivery Method, U.S. Pat. No. 5,041,126, (Aug. 20, 1991). Hillstead, Apparatus and Method for Placement of a Stent within a subject vessel, U.S. Pat. No. 5,019,085 (May 28, 1991) shows a self expanding wire stent mounted on a balloon. Sinofsky, Endovascular Stent and Delivery System, U.S. Pat. No. 5,100,429 (Mar. 31, 1991) shows a rolled stent mounted on a balloon. The Craggstent™, the Wallstent™, and various other commercially available stents also have sharp and irregular surfaces which come into contact with the inner surface of blood vessels during placement. Other environments are also suitable for stent use. For example, the Urolume™ braided urethral stent (American Medical Systems) and the Titan™ titanium tube stent (Boston Scientific) are intended for use in the urethra, and they are visibly sharp-edged stents which must be carefully placed in the urethra to avoid unwanted injury.

A fairly common problem with stent deployment is slippage and early unintentional release of the stent. The stent may pop off the balloon during inflation, or slip backward off the balloon during steering to the intended site of release. Additionally, passage of the exposed stent through the hemostasis valve causes the stent to be dislodged from the balloon. Self-expanding stents are particularly difficult to release in the desired position because they start to expand as soon as the sheath or wires used to retain them are removed. Self-expanding and balloon expanding stents may have to be withdrawn from the blood vessel, backward (proximally) into the delivery sheath, if the stent is misplaced or improperly expanded. After a stent slips backward of the balloon, or if it slips forward off the balloon in a partially expanded condition, the steps necessary to remove the stent can severely damage an artery, and may even require grossly invasive surgery to remove the stent. It has been proposed by Euteneuer, et al., Single Layer Hydraulic Sheath Stent Delivery Apparatus and Method, U.S. Pat. No. 5,445,646 (Aug. 29, 1995) to use several bands of dissolvable material to control the release of a self expanding stent. The bands proposed by Euteneuer are used in conjunction with a sheath which acts as a fairing surface and adds significantly to the outer diameter of the device. The bands themselves add significantly to the outer diameter of the stent assembly and leave exposed sharp and irregular contours of the stent.

SUMMARY OF THE INVENTION

To solve the problems described above and alleviate the potential damage of catheter deployed devices such as stents to the inner wall of blood vessels and other body lumens, the distal end of the catheter, including the irregularly shaped stent, or at least some portion of the stent, is coated with a bioabsorbable and quickly dissolvable (but not too quickly) material. The bioabsorbable material encapsulates the catheter deployed device, providing a smooth autraumatic surface for the device during passage through the vasculature. When used in a stent catheter, the material serves as an adhesive or structural locking mechanism to keep the stent securely attached to the catheter during insertion and expansion. The material dissolves in blood or water, and within a few minutes is completely dissolved away from the device, leaving the device ready for use or placement within the body. The material optimally takes several minutes to dissolve, allowing the surgeon placing the device a reasonable amount of time to snake the device into place. The preferred material is a polysaccharide such as mannitol, sorbitol, sucrose, xylitol, anionic hydrated polysaccharides such as gellan, curdlan, XM-6, xanthan.

DETAILED DESCRIPTION OF THE INVENTIONS

Figure 1:
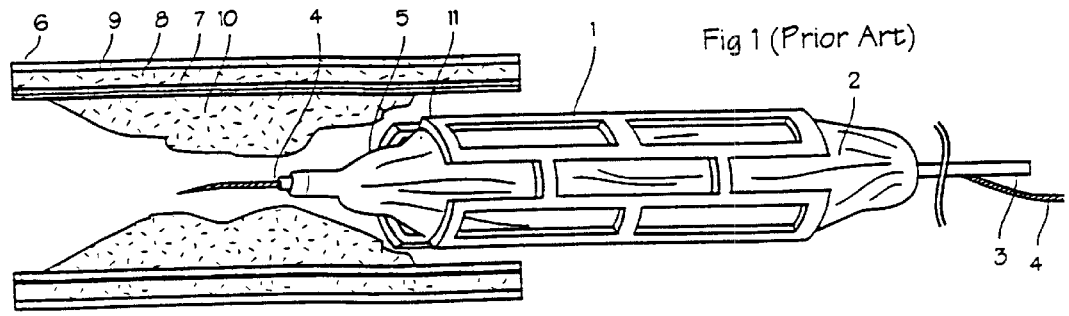
FIG. 1 is a depiction of a typical prior art balloon stent.

FIG. 1 illustrates the typical balloon mounted stent assembly used to delivery stents to the coronary arteries. The stent 1 is a balloon expandable metal stent, such as a Palmaz™ stent or a Palmaz-Schatz™ stent, which closely resemble the illustration. The stent is mounted on an angioplasty balloon 2 or a balloon especially made for stent expansion, and the balloon is in turn mounted on a catheter 3. A guide wire is typically used to assist in placement of the stent catheter, and guidewire 4 is shown in the rapid exchange arrangement, extending from the distal tip 5 of the catheter running proximally through the catheter to the exit point just proximal of the balloon. The catheter used for coronary access will be up to 135 cm long, and the length required for access to other blood vessels will vary according to need. The balloons used for coronary angioplasty are typically 10 to 40 mm in length and 1.5 to 4.0 mm in diameter. The stents are commercially available in various standard sizes, and those used for coronary arteries are about 4 mm to 4 cm in length, while those used in other larger arteries are correspondingly larger. The stent may be made of stainless steel, nickel-titanium, plastics or thermoplastics, balloon deformable nitinol and many other expandable materials.

Self-deploying stents are also commercially available or have been proposed, and these likewise will benefit from use of the inventions have because they have irregular and sharp contours and are subject to premature or uncontrolled release within blood vessels. The Wallstent, Cragg stent, Gianturco stent, and other self expanding wire stents such as Lindenberg, Apparatus for Widening a Stenosis in a body Cavity, Canadian Application 2,019,944 (Oct. 6, 1992) and Lau, Method and System for Stent Delivery, U.S. Pat. No. 5,158,548 (Oct. 27, 1992) are examples of self deploying stents. Several nitinol stents with shape memory have been proposed, such as the McNamara, Nitinol Stent for Hollow Body Conduits, U.S. Pat. No. 5,147,370 (Sep. 15, 1996). All of these stents promise effective treatment for vascular disease, yet each presents sharp and irregular contours to the inner walls of the blood vessels into which they are placed. Thus it can be appreciated that the illustration offered in FIG. 1 is merely demonstrative of the problems presented by stents and other intraluminal devices.

Referring again to FIG. 1, the stent catheter is shown in an intended environment of use, the inside of a blood vessel. The stent must pass through the blood vessel 6 having an inner wall, referred to as the intima 7, a wall referred to as the media 8, and the adventitia 9 on the outer surface of the blood vessel. The blood vessel is partially occluded by the stenosis 10 which is the result of disease or injury. The intima is lined with endothelial cells. Disruption of the endothelial lining of the blood vessel, and damage to the intima, often results in cell proliferation, occlusion and stenosis at the site of the damage. The sharp contours 11 at the distal end of the stent can injure the intima, and cause cell proliferation and stenosis, which is directly counter-productive to therapy. In use, the stent will be pushed into the blood vessel until it bridges the area of the stenosis 10, at which point the balloon will be inflated and the stent will be forced to expand into the stenosis, and will hold the stenosis open to create a patent, lumen in the blood vessel. After the stent is expanded, the balloon is deflated and the catheter is withdrawn. Thus the stent is releasably attached to the catheter. Other stents, such as self-expanding stents, use other means for attaching the stent to the catheter and releasing the stent from the catheter. With all methods of release, inadvertent release and improperly controlled release is a significant problem. Sometimes the stent will slip off the balloon during insertion, and sometimes one end of the stent will expand more quickly than the other, and the stent will squirt off the balloon in a state of partial expansion, or squirt backwards onto the catheter. These problems require removal of the stent, which is quite difficult and can lead to extensive injury of the blood vessel.

Figure 2:
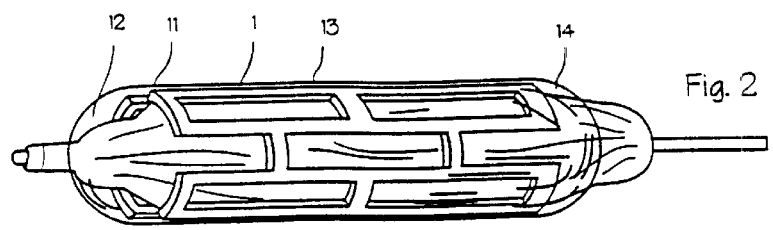
FIG. 2 is a view of a typical prior art balloon mounted stent encapsulated in intra-operatively dissolvable material.

FIG. 2 illustrates the preferred embodiment of the invention. The stent 1 and the balloon 2 are inside a shell or capsule 12 of slowly dissolvable material. The guidewire extends through the capsule, essentially running through a perforation in the distal end 13 of the capsule, and the catheter extends from the proximal end 14 of the capsule, and it is permissible for the balloon to peak out of the capsule, as shown. The material preferably comprises one or more of a number of polysaccharides such as sucrose, mannitol, or sorbitol. These compounds are well known, safe and easy to work with. Sucrose is ordinary table sugar or hard candy, and sorbitol is a well known sweetener used in hard candy (sugarless candy for diabetics), while mannitol is not so well known but has a similar consistency. These materials may be molded onto the stent and balloon to form the capsule, or the stent and balloon may be dipped in melted sucrose, mannitol, or sorbitol or a solution of sucrose, mannitol, or sorbitol. These materials have the consistency of hard candy, and will dissolve in the body in a manner of minutes.

Figure 3:
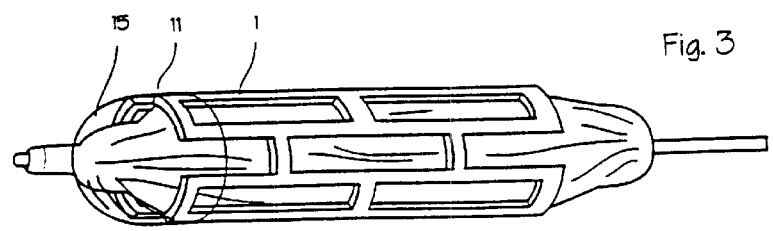
FIG. 3 is a view of a balloon mounted stent secured to the balloon with a distal cap of dissolvable material.

The capsule covers the rough edges of the stent assembly and provides the assembly with a smooth outer surface. Thus, the capsule acts as a fairing surface for the stent assembly and provides a smooth outer surface for the device. This smooth outer surface protects the inner wall of the blood vessel from damage caused by contact with the rough edges of the stent assembly. FIG. 3 shows another embodiment, in which the material does not entirely encapsulate the stent assembly. Instead, a fairing 15 is provided which does not entirely enclose the stent assembly but does provide a smooth surface for the distal end of the stent assembly so that impingement of the stent assembly upon the inner wall of the blood vessel during forward motion of stent in the blood vessel will not injure the blood vessel. The material serves to secure the stent to the balloon, and this helps prevent any unintentional slippage or early release of the stent. As shown in FIG. 3, the fairing has the same outer diameter as the unexpanded stent. The stent and the fairing are isodiametric. Thus the protective feature of the invention may be accomplished without adding to the diameter of the stent assembly. The capsule of FIG. 2 can also be made with the same outer diameter as the stent assembly. It can be seen in view of FIGS. 1, 2 and 3 that the stent assembly may be steered into place within the area of stenosis without the aid of sheaths needed, for example, in U.S. Pat. No. 5,445,646.

Figure 4:
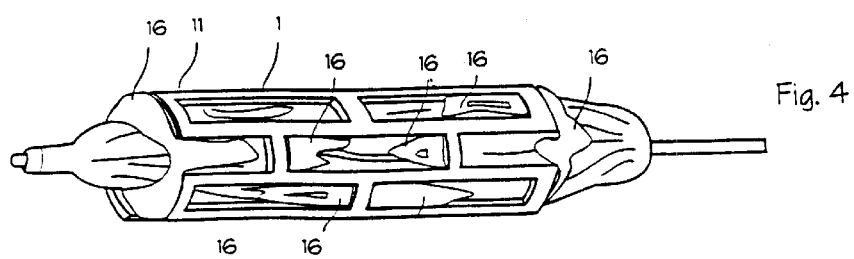
FIG. 4 is a view of a balloon mounted stent secured to the distal end of the insertion catheter with dissolvable adherent material.

In an embodiment shown in FIG. 4, the material is used solely to secure the stent to the balloon. A material such as polysaccharide is applied by dipping or otherwise in amounts sufficient to attach to both the stent and the balloon. Adherent polysaccharide masses 16 of irregular shape are sufficient to hold the stent with sufficient strength to avoid unintentional release of the stent from the catheter used to insert the stent. This secures the stent to the balloon, and may or may not provide significant encapsulation of the stent to protect the blood vessel. The material may be used as a "glue" to secure devices to the catheter. As shown in FIG. 4, the application of the adherent material does not increase the outer diameter of the stent assembly. It also slightly smoothes the sharp edges without adding to the outer diameter of the stent assembly.

Figure 5:
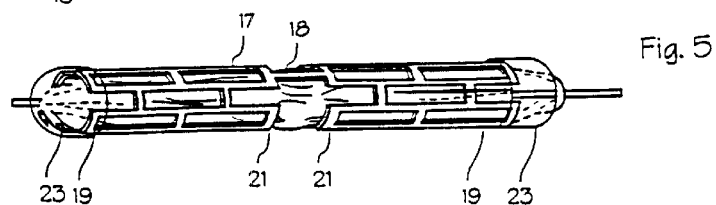
FIG. 5 is a view of a multi-segment stent secured to a balloon with an intra-operatively dissolvable material.

When used for stents and other expandable devices, a material with sufficient mechanical strength, such as sucrose or sorbitol, can be used to control the expansion of the device by applying the material over areas where delayed expansion is desired. Thus, the expansion of a stent in a blood vessel may be controlled to occur uniformly or unevenly from the distal end to the proximal end by applying the material in appropriate areas of the stent. FIG. 5 shows a Palmaz-Schatz™ stent 17 with two sections of expandable metal stent connected with a bridge 18. This construction is referred to as an articulated stent. Most, if not all, balloon expandable stents tend to expand at the ends first, because the balloon extends beyond the ends of the stent. Thus the unrestrained end portions of the balloon expand first. The balloon expansion then propagates towards the center of the balloon. The distal end portion 19 and the proximal end portion 20 of the stent expand first, followed by expansion of the middle of the stent 21. This situation is referred to as "dog-boning," in which the unsecured distal and proximal ends of the stent expand before the central portion, and this can cause the stent to dislodge from the balloon, leading to inaccurate placement or incomplete expansion of the stent. Deploying the stent with the fixation/fairing surface in place, and not yet dissolved, at the ends of the stent will cause the stent to expand in the middle portion first, followed by expansion which propagates towards the distal and proximal ends. In this method, there is no need to wait for the soluble material to dissolve, and the stent may be expanded before the dissolvable material is fully dissolved, and the material is left in the body for eventual dissolution and absorption.

As shown in FIG. 5, the fairing caps 22 and 23 provide additional mechanical strength to the distal and proximal ends of the articulated stent, thus preventing or minimizing the tendency of these stents to dog-bone or otherwise expand in a non-uniform manner. Other arrangements of the dissolvable material used to control stent expansion are also useful. For example, to ensure that the distal end of the balloon expandable stent or self expanding stent expands before the proximal end, the material may be applied only over the proximal end, or more heavily over the proximal end, of the stent. This will ensure distal first expansion of the stent, so that any slippage occurs in the proximal direction, thus facilitating removal of the stent in the case of incomplete expansion, or ensuring proper distal placement for stents subject to foreshortening.

The material used for the capsule or fairing of the stent assembly may be any material which has sufficient material strength to stay intact during passage of the entire assembly through the blood stream, will not dissolve too quickly so as to provide a reasonable amount of time to pass the assembly through the blood stream, but will dissolve during a reasonable time in the blood stream to allow unhindered deployment and expansion of the stent. Thus, it is not necessary that the material be a solid, and a semi-solid or gelatinous material will suffice. It is also not necessary that the entire mass of the material dissolve before the stent is expanded, so long as the material is or becomes pliable or yieldable (the material can be brittle or ductile) so as to allow expansion of the stent. It is preferred that the material be biocompatible, at least to the extent that it does not cause any severe reactions itself, such as thrombosis, unwanted vasorestriction, etc. A material having some known complications or some level of toxicity may be acceptable. The material may be pyrogenic or not.

A great many compositions can be used for the capsule or fairing of the stent assembly, provided that the composition be dissolvable within an appropriate amount of time. Compositions which satisfy this criteria include both natural and synthetic substances. Preferred natural compositions include simple and complex carbohydrates, proteins, lipids and combinations thereof. Carbohydrate compositions, however, are generally preferred over protein and lipid compositions because they tend to be less immunoreactive. Disaccharides of six carbon simple sugars (hexatols) are particularly preferred, including sucrose, mannitol and sorbitol, although carbohydrates including sugars of other sizes are contemplated. Natural compositions need not be native to any particular species, and may include mucoid substances, pectins, gels, soluble starches, carrageenan and furcelleran and agar. Synthetic compositions may also be used for the capsule material, fairing material or adherent material, including derivatives of natural compositions such as algenic acid, hydrated gels and the like, and also biocompatable polymers and oligomers such as dextrans, dextranes and dextrins, polyethylene glycol (PEG), polyethylene oxide, polypropyline oxide, polyvinylpyrrolidine, polyvinyl acetate and polyvinyl alcohol.

It is contemplated that the rate at which a capsule or fairing composition dissolves can be regulated by regulating the degree of cross-linking within the composition. For example, agar can be cross-linked in solution through the addition of polyvalent cations Ca++ or Mg++, and the degree of cross-linking can be regulated by the relative molarity of cations present. It is also contemplated that capsule or fairing compositions could be built up in layers wherein the different layers have varying degrees of cross-linking.

The capsule or fairing composition may be present in a variety of forms. For example, carbohydrates and carbohydrate derivatives may be used in their sugar, sugar alcohol, or other forms. The capsule or fairing composition may also be solid or semi-solid as in the case of a gel, and may be hydrated to modify the hardness.

Other suitable materials include carbohydrates such as starch and sugars, polysaccharides such as mannitol, maltitol, sorbitol (and any other hexatol), xylitol, fructose, sucrose, dextrose and glucose and glucosamine, lactose, anionic hydrated polysaccharides such as gellan, curdlan, XM-6, xanthan, etc., seaweed polysaccharides such as agar, algin, carrageenan or furcelleran and cellulose derivatives such as alkyl cellulose, hydroxymethyl cellulose, etc. The materials generally used for gel-cap coverings of pills may be used. Various salts such as sodium chloride, potassium chloride, and sodium carbonate may be used. Polyvinylpyrrolidone, polyvinyl acetate, acetates generally, and other materials will also be useful. Gums including gum arabic and tragacanth gum may be used.

In short, the variety and number of useful compounds is far too long to list, and it will be understood that any material or combination of material with sufficient material strength, optimal disintegration time frame within the body, and acceptable level of harmful side effects may be used to create embodiments of the invention covered by the claims. Furthermore, the many compounds which will timely disintegrate within the body need not technically be "soluble" as that term is used by chemists. In ordinary language, to dissolve means to disperse or disappear, and by use of the terms soluble and dissolve, and it is intended to include dissolution, dispersion or decomposition within the body via any mechanisms. Decomposition may occur by dissolving, hydrolysis, glycolysis, pyrolisis, emulsification, melting or even radiolysis or photolysis. Any physical, chemical or biological mechanism by which the material will decompose and permit use of the device within a reasonable intraoperative time frame may be beneficially employed as a fairing or encapsulation material. Thus the words dissolve, disintegrate and decompose are used synonymously in this specification and the claims to encompass any form of dissolution, disintegration or decomposition. The same generality applies to the final disposition of the material in the body, whether it be absorbed, resorbed or disposed of by the body through some other means. There may be technical distinction in the scientific definitions of these words, but the general concept that these materials do not remain intact in the blood stream to cause later occlusions may be conveyed by the use of the terms resorbtion, absorption and the like.

The time to dissolution in the body can be controlled by choice of material, by the thickness applied to the stent assembly, and by mixing of different compounds. Where stents assemblies are to be deployed into large blood vessels such the aorta, a thick layer of more quickly dissolving material may be applied, whereas in a stent assembly for use in the coronary arteries which are very small, a capsule of just slightly greater diameter than the unexpended stent may be fabricated with a very slowly dissolving material such as a starch. For general use in peripheral arteries or other lumens such as the urethra, esophagus, fallopian tubes, colon, etc., a mid range of solubility may be preferred. In practice, a range of dissolving time from about one minute to thirty minutes will be most useful.

The material applied will preferably dissolve intraoperatively. Thus, if it is expected that surgeons will typically be able to steer a stent from the percutaneous access site in the femoral artery to the coronary arteries in five minutes, then the amount and type of material used to encapsulate the stent will be adjusted so that it dissolves away in about five minutes. If placement is accomplished quickly, as may be done with a rapid exchange balloon catheter which is tracked over a guide wire, then the material used to form the fairing or capsule may be made thinner so as to allow for quick dissolution in the blood stream.

In an exemplary use, the balloon mounted stent catheter will be inserted percutaneously or through a cut down in a large peripheral vessel such as the femoral artery. The stent will be maneuvered through the vasculature to the desired position, which may be the coronary arteries, the peripheral arteries or the aorta. The stent must be inserted into the peripheral vessel at an angle, and will be steered through several tortuous turns on its way to the target site. Once in place near the target site, the stent may be pushed and pulled to orient it precisely within the artery. Opportunity for injurious contact with the intima occurs at every turn, and upon each movement of the stent. However, with the capsule surrounding the stent, any contact between the stent assembly and the intima will be prevented by the capsule, and the smooth capsule surface will not harm the intima. Thus, the chance of post-operative thrombus formation, stenosis or plaque formation at the site of injury caused by the stent assembly is minimized. After the stent is positioned as desired in the blood vessel, the capsule will dissolve to the point where stent expansion may be accomplished by inflating the balloon. (It will be appreciated that the many self-expanding stents will self expand when the capsule dissolves.) If the stent is expanded while the capsule material is still partially intact, the material will eventually dissolve. It will prove useful in some operations to expand the stent without waiting for the soluble material to dissolve first. If it is desired to expedite dissolution of the capsule material, saline solution, enzyme solution (for example amylase) or other appropriate solution may be flushed around the stent through an introducer catheter used in conjunction with the balloon catheter. After placement of the stent, including verification of the placement with an ultrasound catheter or angiogram, the catheter may be withdrawn from the body.

In another exemplary use, fixation and fairing attributes are used to protect a stent from dislodgment during placement in the liver and to protect a dissected or man-made passageway in the body from damage. Transjugular intrahepatic porto-systemic shunting (TIPS) is one such operation. In the TIPS procedure, surgeons use endovascular tools to punch a hole through the liver parenchyma, and provide a conduit that is not naturally occurring. This provides a passageway for flow of blood from the high pressure side of the liver to the systemic side of the liver without having to filter through the liver. The operation is used as a stop-gap measure for patients awaiting liver transplant, and for other purposes. The operation often entails placement of a stent, graft or valve within the conduit created by the surgeon. Stents, grafts or valves so placed may advantageously be fixed to the delivery catheter with the dissolvable adherent material in a fashion similar to that illustrated in FIG. 4, and may be provided with a soluble fairing or capsule. In this use, the vessel of the body includes a conduit or tunnel created by surgeons that is not a natural vessel or lumen of the body.

While providing a smooth outer surface for devices in the body, the soluble capsule serves other purposes also. Upon entry into the body, the materials such as sucrose, mannitose and sorbitol will become slippery, and thus provide a lubricating surface. The material may be mixed with a number of other compounds which provide pain killers, anti-coagulants and anti-thrombus agents and any other useful compound.

While the encapsulation and fairing techniques have been described in relation to the problem of intima damage caused by intravascular catheters, and illustrated with the example of an intravascular stent, they will be beneficial in any number of environments and with any number of instruments. Sharp and irregularly contoured devices such as atherectomy cutters, ultrasound catheters, venous filters, ablation electrodes and antennas, electrocautery devices, and endoscopic instruments such as endoscopes, graspers and cutters, biopsy instruments and many others will benefit from the protective covering. These instruments may be used in environments such as the esophagus and stomach, the urethra, bladder and ureter, the fallopian tubes, the large and small intestines, the colon, etc. In any situation in which an instrument must be passed into the body and may unintentionally damage organs and tissue in the insertion pathway, the instrument may be coated with an intra-operatively dissolvable material so that the insertion pathway is protected from damage during insertion.

While the preferred embodiments of the devices and methods have been described, they are merely illustrative of the principles of the invention. Other embodiments and configurations may be devised without departing from the spirit of the inventions and the scope of the appended claims.

I claim:

1. A device for treating a lumen of the body comprising:
   a catheter having a distal end for insertion into the lumen of the body;
   a stent mounted on the distal end of the catheter, said stent characterized by a distal end, a proximal end, and a center portion, said stent being compressed in an small diameter insertion configuration; and
   a fairing cap covering the distal end of the stent, said fairing cap comprising a dissolvable material, said fairing cap terminating proximally from the distal end of the stent so as to leave the center portion of the stent uncovered by the cap.

2. The device of claim 1 wherein the fairing cap is comprised of a hard sugar which is dissolvable in the body within an intra-operative time frame.

3. The device of claim 1 further comprising a balloon disposed on the distal end of the catheter, wherein the stent is disposed over the balloon.

4. A device for treating a lumen of the body comprising:
   a catheter having a distal end for insertion into the lumen of the body;
   a stent mounted on the distal end of the catheter, said stent characterized by a distal end, a proximal end, and a center portion, said stent being compressed in an small diameter insertion configuration;
   a fairing cap covering the distal end of the stent, said fairing cap comprising a dissolvable material, said fairing cap terminating proximally from the distal end of the stent so as to leave the center portion of the stent uncovered by the cap; and
   a second fairing cap covering the proximal end of the stent, said second fairing cap terminating distally of the proximal end of the stent so as to leave the center portion of the stent uncovered by the cap.

5. The device of claim 4 wherein the first and second fairing caps are comprised of a hard sugar which is dissolvable in the body within an intra-operative time frame.

6. The device of claim 2 wherein the first and second fairing caps are isodiametric with the stent in its small diameter insertion configuration.

7. A device for treating a lumen of the body comprising:
   a catheter having a distal end for insertion into the lumen of the body;
   a stent mounted on the distal end of the catheter, said stent characterized by a distal end, a proximal end, and a center portion, said stent being compressed in an small diameter insertion configuration;
   a fairing cap covering the distal end of the stent, said fairing cap comprising a dissolvable material, said fairing cap terminating proximally from the distal end of the stent so as to leave the center portion of the stent uncovered by the cap; and
   wherein the fairing cap is isodiametric with the stent in its small diameter insertion configuration.

* * * * *